Figure 1:
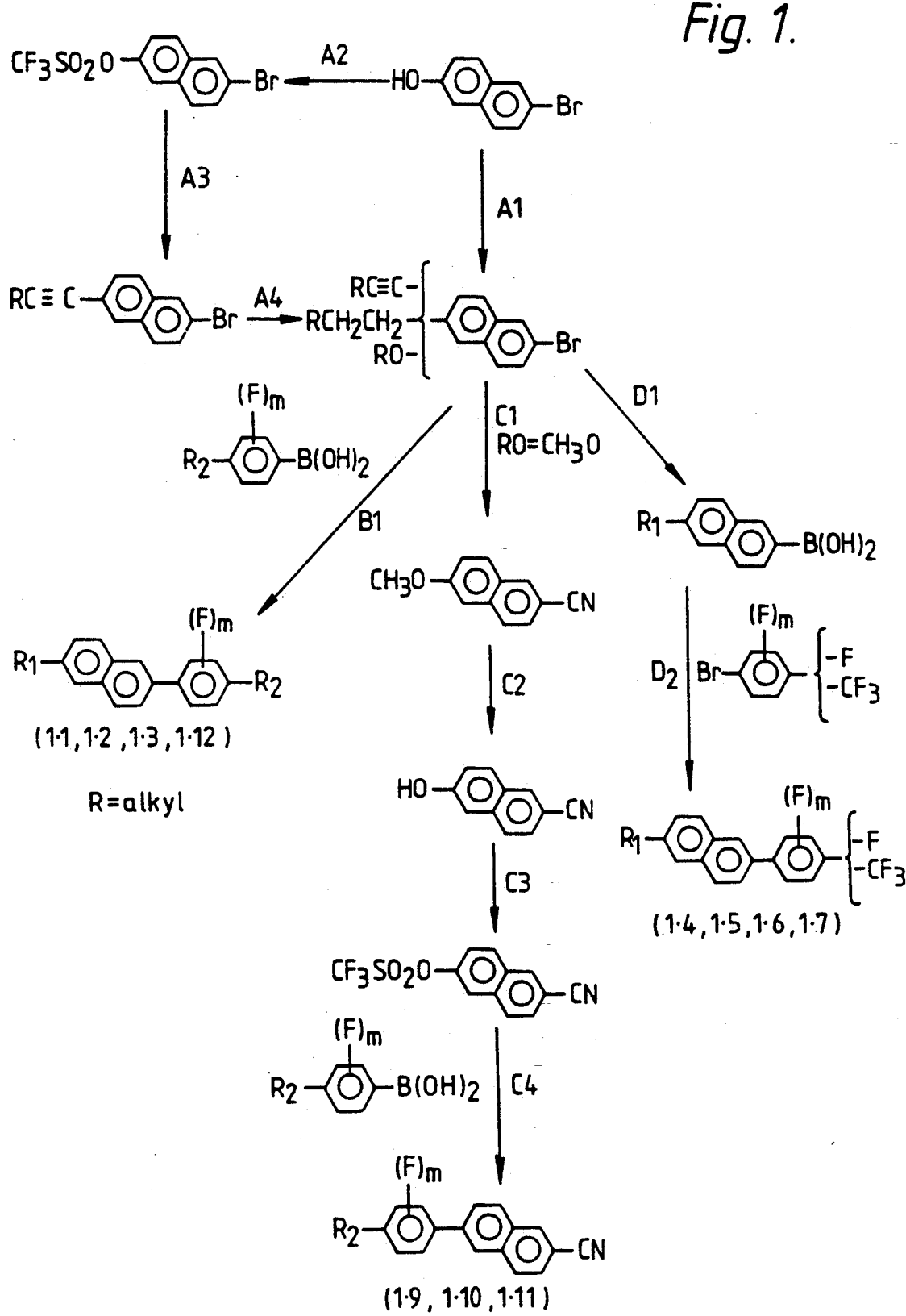

United States Patent [19]

Gray et al.

[11] Patent Number: 5,252,253

[45] Date of Patent: Oct. 12, 1993

[54] PHENYL NAPHTHALENES HAVING LIQUID CRYSTALLINE PROPERTIES

[75] Inventors: George W. Gray, Wimborne; Kenneth J. Toyne, Hull; David Lacey, Hull; Michael Hird, Hull, all of United Kingdom

[73] Assignee: The Secretary of State for Defence in Her Britannic Majesty's Government of the United Kingdom of Great Britain and Northern Ireland, London, England

[21] Appl. No.: 721,440

[22] PCT Filed: Jan. 16, 1990

[86] PCT No.: PCT/GB90/00069

§ 371 Date: Jul. 16, 1991

§ 102(e) Date: Jul. 16, 1991

[87] PCT Pub. No.: WO90/08119

PCT Pub. Date: Jul. 26, 1990

[30] Foreign Application Priority Data

Jan. 16, 1989 [GB] United Kingdom ............. 8900870.0
Nov. 10, 1989 [GB] United Kingdom ............. 892541.8

[51] Int. Cl.$^5$ .................... C09K 19/32; C07C 41/00; C07C 255/00; C07C 19/08
[52] U.S. Cl. ................. 252/299.62; 585/26; 558/425; 568/632; 570/129
[58] Field of Search ............ 252/299.62; 570/129; 558/425; 585/26; 568/632

[56] References Cited

U.S. PATENT DOCUMENTS

| | | | |
|---|---|---|---|
| 4,331,613 | 5/1982 | Marhold et al. | 260/544 B |
| 4,386,007 | 5/1983 | Krause et al. | 252/299.62 |
| 4,432,885 | 2/1984 | Petrzilka et al. | 252/299.61 |
| 4,438,268 | 3/1984 | Zaschke et al. | 544/315 |
| 4,886,619 | 12/1989 | Janulis | 252/299.1 |
| 5,072,021 | 12/1991 | Nakatsuka et al. | 560/56 |
| 5,082,587 | 1/1992 | Janulis | 252/299.01 |
| 5,146,025 | 9/1992 | Koyama et al. | 585/412 |

FOREIGN PATENT DOCUMENTS 2949080 6/1981 Fed. Rep. of Germany.
0141527 8/1984 Japan.

*Primary Examiner*—Robert L. Stoll
*Assistant Examiner*—C. Harris
*Attorney, Agent, or Firm*—Nixon & Vanderhye

[57] ABSTRACT

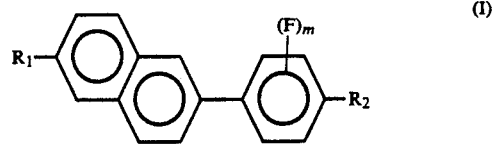

Novel phenyl naphthalenes of general formula (I) wherein $R_1$ and $R_2$ are selected from $C_{1-15}$ alkyl, alkoxyl, perfluoroalkyl, perfluoroalkoxyl and alkynyl, $R_1$ may also be CN and $R_2$ may also be fluorine or NCS; m is 0, 1 or 2 provided that if $R_1$ is alkyl or alkoxyl and $R_2$ is alkyl, alkoxyl, perfluoroalkyl or CN then m is 1 or 2. These have liquid crystalline characteristics and may be used as constituents of both nematic and smectic C liquid crystal materials.

17 Claims, 1 Drawing Sheet

PHENYL NAPHTHALENES HAVING LIQUID CRYSTALLINE PROPERTIES

This invention relates to novel phenyl naphthalenes having liquid crystalline properties and to their use in liquid crystal materials and devices.

Liquid crystal materials and devices exploit the electro-optical properties of nematic or cholesteric (N or N*), or smectic (S) in particular chiral smectic C (Sc*) or smectic A (SA) phases. The most common type of liquid crystal materials in use are those which show a nematic phase and these are extensively used in, for example, watches, clocks, calculators, electronic displays etc.

Liquid crystal materials which show a ferro-electric Sc* phase are useful in fast switching displays such as television or VDU screens as the Sc* phase can be switched in a few milliseconds or even microseconds. The principle of Sc* switching is described inter alia by N. A. Clark and S. T. Lagerwall in App-Phys Lett 36 (1980) 899.

Materials which show an SA liquid crystal phase may be used in display devices which exploit the electroclinic effect.

Liquid crystal materials desirably are easy to prepare, show liquid crystal phases which persist over a wide temperature range which preferably includes room temperature and useful physics-chemical properties such as birefringence. For some applications of liquid crystal materials a high birefringence is sought, e.g. in the so-called "electrically controlled birefringence" (ECB) effect device (see, for example, M. F. Schieckel and R. Fahrenshon App Plays Lett (1971), 19, 2912), in thin film transistors (TFT) or supertwist twisted nematic (STN) devices. It is rare for all the requisite desirable properties to be found in a single liquid crystalline compound and generally liquid crystal materials consist of mixtures of component compounds. Very many liquid crystalline compounds suitable for such uses are known and will be apparent to those skilled in the art.

Some liquid crystalline compounds are known, based upon the phenyl, naphthalene system, i.e.:

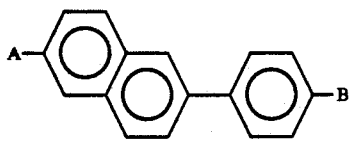

For example, Bull Soc Chim F: (1975) 11-12(2) 2521-6 describes compounds where A is alkoxy and B is alkyl or alkoxy and Helv Chim Acta (1985) 68(5) 1406-26 describes those in which A is alkyl or alkoxy and B is cyano or trifluoromethyl. The present inventors have applied developments in synthetic organic chemistry to investigate the phenyl-naphthalene system further with the object of identifying novel compounds which provide improved or alternative liquid crystalline characteristics.

According to this invention, phenyl-naphthalenes of general formula I are provided:

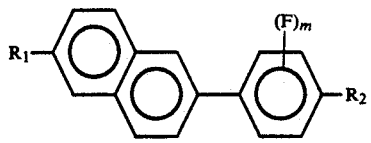

formula I wherein $R_1$ and $R_2$ are selected from $C_{1-15}$ alkyl, alkoxyl, perfluoroalkyl, perfluoroalkoxyl and alkynyl, $R_1$ may also be CN and $R_2$ may also be fluorine, CN or NCS, m is 0, 1 or 2 provided that if $R_1$ is alkyl or alkoxyl and $R_2$ is alkyl, alkoxyl, perfluoroalkyl or CN then m is 1 or 2.

The preferred embodiments of the invention discussed below are inter alia chosen with respect to ease of preparation and their liquid crystal properties, particularly with respect to suitability for use in high birefringence nematic or ferro-electric Sc* liquid crystal materials.

Preferably for use in nematic materials alkyl or alkoxyl substituents $R_1$ and/or $R_2$ contain 1-8 carbon atoms and for use in smectic materials 3-12. For use in nematic materials compounds having $R_1$ as alkyl or alkoxyl and $R_2$ as fluorine; or $R_1$ as alkynyl and $R_2$ as alkyl or alkoxyl, or $R_1$ as CN and $R_2$ as alkyl, alkoxyl or alkynyl are preferred. Preferably for smectic C materials $R_1$ and $R_2$ are selected from n-alkyl or n-alkoxyl, m is 1 or 2, especially 2, preferably with the fluorines in the 2, 3 positions.

Preferred overall structures for the phenyl naphthalenes of formula I are listed below:

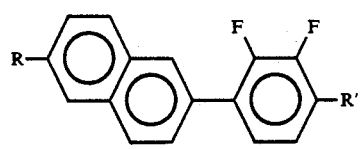

1.1

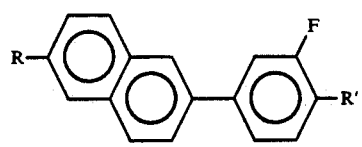

1.2

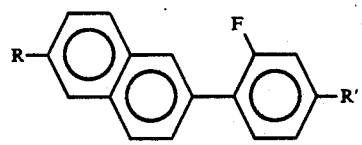

1.3

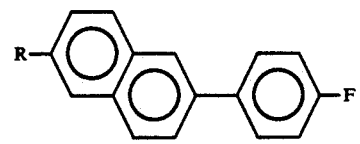

1.4

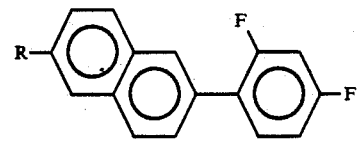

1.5

-continued

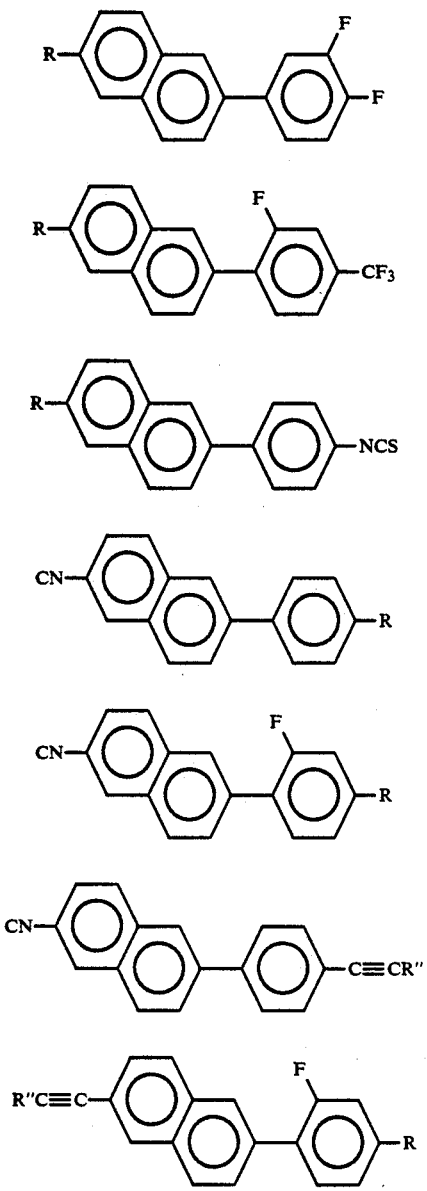

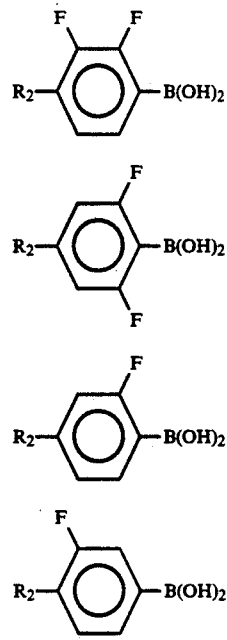

Where R and R' are independently alkyl or alkoxyl and R" is alkyl.

For use in nematic materials structures 1.4, 1.5, 1.6, 1.9, 1.10, 1.11 and 1.12 are preferred. For smectic materials structure 1.1 is preferred.

Phenyl-naphthalenes of formula I may be prepared by generally applicable routes A to D shown in FIG. 1 of the accompanying drawings. In these routes the reaction conditions of the individual steps are well known but the overall combination of steps to form the end product is novel. Compounds in which $R_2$ is NCS, e.g. 1.8 are preferably prepared by initially incorporating an amino group into the molecule as $R_2$, for example, coupling the boronic acid of step D1 with para-bromoaniline and then converting the amino group into an isothiocynanate. Ways of doing this will be apparent to those skilled in the art.

Preparative routes to intermediates of formula:

where $R_2$ is alkyl or alkoxyl are described in published WO 89/02425 and WO 89/08687 among others.

The invention also provides a liquid crystal material being a mixture of at least 2 component compounds, at least one of which is a phenylnaphthalene of formula I. This material may show a nematic or smectic (e.g. smectic C, $S_c^*$ or $S_A$) liquid crystal phase.

In particular many phenyl-naphthalenes of formula I have a high birefringence, making them suitable for applications in which this characteristic is required, as discussed above. In particular, compounds of formula I which contain an alkyne group may have a high birefringence. Although some have rather high melting points this can in some cases be usefully reduced by introducing one or more lateral fluorosubstituents on the phenyl ring, e.g. as in 1.1, 1.2, 1.3, 1.5, 1.6, 1.7, 1.10 and 1.12. Phenyl-naphthalenes of formula I may be used as components of nematic liquid crystal materials together with other known nematic liquid crystalline compounds especially, for example, compounds of general formulae IIA, B and C, in particular IIA: (F) (F)

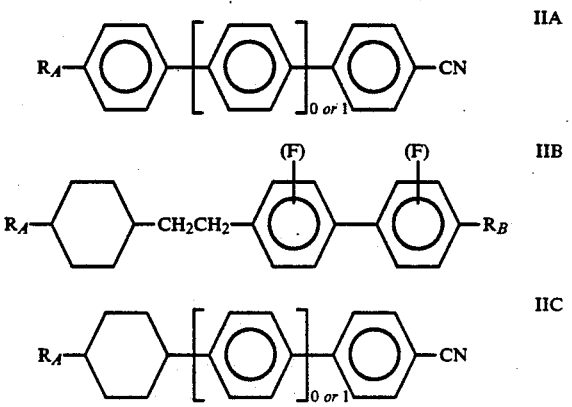

Where $R_A$ and $R_B$ are independently $C_{1-10}$ n-alkyl or n-alkoxy and (F) indicates that one of the rings carries a fluoro substituent. Other known compounds which may be usefully included as components of nematic liquid crystal materials include those described, for example, in GB 1551043, GB 1556994, GB 1592147, GB 1587819, GB 1603076, GB 2011940, GB 2023136, GB 2027708, GB 2027027, GB 2063250, GB 2063250, GB 2071649, GB 2070594, GB 2071131, GB 2081707, GB 2079275, GB 2080820, GB 2089345, GB-A-8203798, EP 0060646, GB 2111974, U.S. Pat. No. 4,482,472, GB 2118934, U.S. Pat. No. 4,506,957, GB 2121406, EP-A-83303348.3, GB 2134110, EP-A-8430494.3, EP-A-84303240.0.

For use in applications where a high birefringence is desirable. The mixture may also contain one or more fluorinated cyanobiphenyls or terphenyls of formula IID:

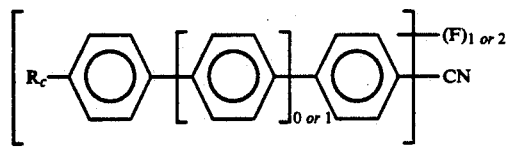

where $R_c$ is $C_{1-10}$ n-alkyl or n-alkoxyl and the fluoro substituent(s) may be in any one or 2 of the available substitution positions. Compounds of formula IID are known (PCT/GB 89/00647) and their inclusion can further increase the birefringence.

A nematic liquid crystal material of this invention may also contain one or more optically active compounds (especially the biphenyl of formula IIA in which $R_A$ is (+)-2-methylbutyl) to induce a cholesteric phase and one or more pleochroic dyes.

Typically but not exclusively, a nematic liquid crystal material may contain 5–50% by weight of other known nematic materials. Optically active compounds and/or pleochroic dyes if present will generally be present at up to 1% by weight at molt.

Phenyl-naphthalenes of formula I may be used as components of smectic C mixtures. Compounds of structure 1.1 above are particularly preferred for this use as they show Sc phases which persist over a wide temperature range and their use can result in Sc* mixtures which show fast, e.g. microsecond, switching speeds.

Other compounds which show an Sc phase to provide a mixture having improved properties relative to the individual component compounds. Preferred known compounds which show an Sc phase and may be used in this way include the known compounds of formula IIIA and IIIB:

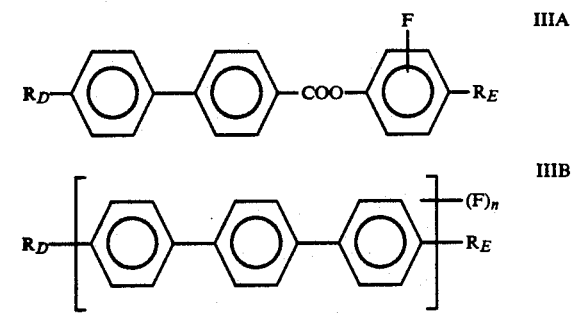

where $R_D$ and $R_E$ are independently $C_3$–$C_{12}$ n-alkyl or n-alkoxy and n in formula IIIB is 1 or 2. In formula IIIA the fluorine substituent is preferably adjacent to the ester linkage. In formula IIIB when n is 1 the fluorine is preferably on the central ring and when n is 2 the fluorines are preferably in the 2, 3- or 2', 3'-positions.

The Sc mixture may also include additives which suppress undesirable smectic phases such as SB, or which promote the phase transition sequence $S_C$–$S_A$ at higher temperatures. Examples of additives which may be used for these purposes are compounds of formula IIIC or IIID:

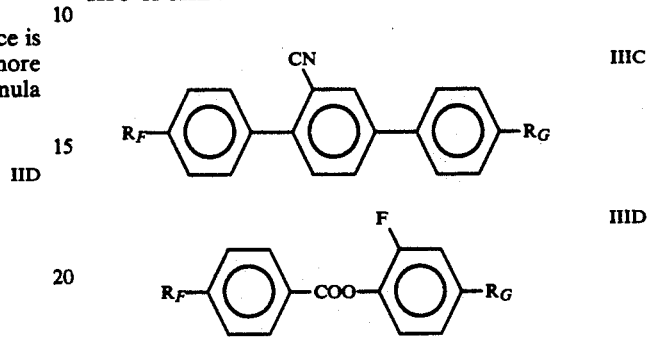

wherein $R_F$ and $R_G$ are independently $C_1$–$C_{12}$ n-alkyl or n-alkoxy.

When the mixture is intended to show an Sc* phase it is necessary to include one or more optically active compounds, i.e. "dopants" in the mixture. A large variety of such dopants is known, for example, the compounds described in EP-A-0110299, which are esters of 1-methyleptanol, e.g.:

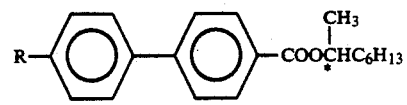

where R is $C_{1-15}$ n-alkyl or alkoxyl.

Particularly preferred dopants are however the known compounds containing an asymmetrically substituted group IV:

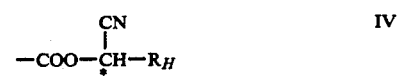

where $R_H$ is cycloalkyl, a cyclic terpenoid ring system or $C_{1-8}$ n-alkyl or branched alkyl, especially $C_{1-4}$ n-alkyl or branched alkyl having a formula:

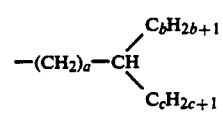

where a is 0 or an integer 1–6 and b and c are independently 1–6. In such compounds $R_H$ is preferably methyl, $CH(CH_3)_2$ or a camphor residue.

Suitable and preferred examples of such dopants are described in WO 87/07890 and PCT/GB 88/01111.

Another preferred class of optically active dopants are the naphthyl esters disclosed in WO 87/06577, e.g. V:

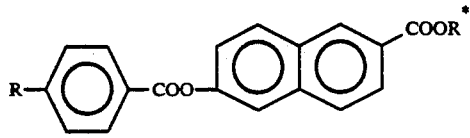

where $R_f$ is $C_{1-12}$ n-alkyl or n-alkoxyl and R* is 1-methylyheptyl.

Advantageously the Sc* mixture may contain at least 2 optically active dopants having opposite helical twisting effects.

Typically but not exclusively, a ferroelectric Sc* mixture of this invention may contain 1–99% by weight of compounds of formula I, plus 0–99% by weight of other compounds which show an Sc phase, plus 0–30% by weight of additives, plus 1–20% by-weight of optically active compounds.

Liquid crystal materials of the invention may be used in display devices of known construction and method of operation. Typically an electro-optical display device will consist of 2 substrates between which a layer of the liquid crystal material may be sandwiched. At least one of the substrates is optically transparent and both have electrodes which are preferably made of a transparent material on their opposing faces. By applying an electric field across the layer of liquid crystal material via the electrodes an electro-optic effect is achieved which may be viewed directly or preferably through one or more polarising filters.

Having a high birefringence nematic materials of this invention may be particularly suitable for use in ECB effect devices. They may also be particularly suitable for use in polymer dispersed liquid crystal (PDLC) materials in which small droplets of a liquid crystal material are dispersed within a matrix of a transparent polymer.

Non-limiting example illustrating this invention are now described with reference to FIG. 1 which shows schematic routes A, B, C and D to phenylnaphthalenes of formula I In each synthesis drying was by magnesium sulphate.

EXAMPLE 1—ROUTE A USED TO PREPARE

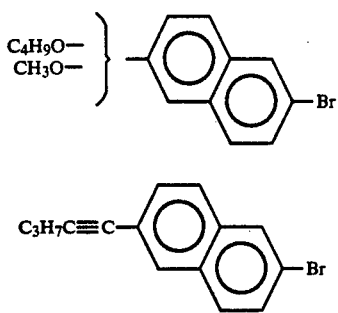

Step A1 (R=butyl)

A solution of 1-bromobutane (50g 0.36 mol) in acetone (90 ml) was added dropwise to a stirred refluxing mixture of 2-hydroxy-6-bromonaphthalene (40 g 0.18 mol) and potassium carbonate (51 g 0.37 mol) in acetone (1L). The stirred mixture was heated under reflux for 24 hours. The potassium carbonate was filtered off, water was added to the filtrate and the product was extracted into ether (twice). The combined ethereal extracts were washed with water, 5% sodium hydroxide, water and dried. The solvent and the excess of 1-bromobutane were removed in vacuo to yield an off-white powder which was recrystallised from ethanol. Yield 32.2 g (64%) mp 52°–53° C.

In an alternative method where R=methyl, dimethyl-sulphate (33.80 g 0.268 mol) was added to a stirred solution of 2-hydroxy-6-bromonaphthalene (50 g 0.224 mol) and potassium hydroxide (15 g 0.268 mol) in water at room temperature. The stirred mixture was heated at 70° C. for one hour and stirred at room temperature over night. The produce was filtered off, washed with 10% sodium hydroxide, water and dried well and then extracted into dichloromethane. The organic extract was washed with 10% sodium hydroxide, water and dried. The solvent was removed in vacuo to give a colourless solid. Yield 50.9 g (96%) mp 108°–110° C.

Step A2

A solution of N-phenyltriflamide (4.93 g 0.0138 mol) in dry dichloromethane (25 ml) was added dropwise to a stirred, cooled (−78° C.) solution of 2-hydroxy-6-bromonaphthalene (2.80 g 0.0126 mol) in dry dichloromethane (40 ml) and dry triethylamine (2.55 g 0.025 mol) under dry nitrogen. The stirred mixture was allowed to warm to room temperature overnight and was then washed with aqueous sodium carbonate and the separated aqueous layer was washed with dichloromethane. The combined organic extracts were washed with water and dried. The solvent was removed in vacuo and the residue was purified by column chromatography (silica gel/dichloromethane) to give a colourless solid. Yield 7.20 g (99%) mp 93°–94° C.

Step A3

A solution of n-butyllithium (6 ml 2.5 m in hexane) was added dropwise to a stirred, cooled (−5° to 0° C.) solution of pent-1-yne (1.02 g 0.015 mol) in dry THF (10 ml) under dry nitrogen. This mixture was stirred at room temperature for 15 minutes and a solution of 6-bromonaphth-2-yl triflate (from Step A2) (4.80 g 0.0135 mol) in dry THP (20 ml) was added dropwise at −5° to 0°C. followed by the addition of tetrakis (triphenylphosphime) palladium (o) ("TTPP") (0.5 g 0.43 mmol). The mixture was heated under reflux (90° C. for hours) and then poured into 10% hydrochloric acid. The product was extracted into ether (twice) and the combined ethereal extracts were washed with aqueous sodium hydrogen carbonate and dried. The solvent was removed in vacuo and the crude product was purified by column chromatography (silica gel/petroleum fraction (bp 40°–60° C.) to give a colourless solid. Yield 2.10 g (57%).

This product could be used directly in Steps B1, C1 and D1 or could be reduced using known methods to convert the alkynyl group to an alkyl group.

EXAMPLE 2—ROUTE B USED TO PREPARE

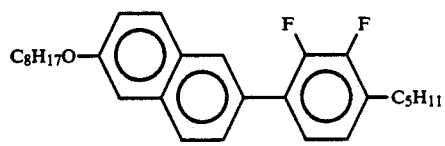

Step B1

A solution of 2-octyloxy-6-bromohaphthalene (1.75 g 5.22 mol) prepared via Step A1 above in ethanol (15 ml) was added to a stirred solution of 1-pentyl-2, 3-difluoro phenylboronic acid (known) (1.60 g 7.02 mmol) and TTPP (0.312 g 0.27 mol) in benzene (30 ml) and 2M sodium carbonate (30 ml) at room temperature under dry nitrogen. The stirred mixture was heated under reflux (100° C.) for 23 hours. The product was extracted twice into ether and the combined ethereal extracts were washed with brine and dried. The solvent was removed in vacuo and the residue was purified by column chromatography (silica gel/petroleum fraction (bp 40°–60° C.) -dichloromethane 10:1) to give a colourless solid which was recrystallised from ethanol-ethyl acetate (20:1) to yield colourless crystals. Yield 1.90 g (83%).

By an analogous procedure the compound

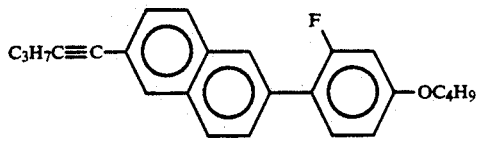

was prepared, using the product of Step A3 and known 1-butyloxy-3-fluorophenylboronic acid. Yield 63%.

EXAMPLE 3—ROUTE C USED TO PREPARE

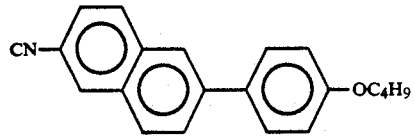

Step C1

A mixture of 2-methoxy-6-bromonaphthalene (12 g 0.051 mol) and copper (I) cyanide (5.26 g 0.059 mol) in dry DMF (75 ml) was heated at 185° C. for 5 hours. The cooled mixture was poured into 10% hydrochloric acid and the product was extracted into ether. The insoluble salts were filtered off and the separated aqueous layer was washed with brine and dried. The solvent was removed in vacuo and the residue was purified by column chromatography (silica gel/petroleum fraction (bp 40°–60° C.) -dichloromethane 1:2) to give a pale yellow solid. Yield 7.60 g (81%) mp 103°–104° C.

Step C2

A solution of boron tribromide (24 g 10.0 ml 0.0956 mol) in dry dichloromethane 200 ml was added dropwise to a stirred, cooled (−78° C.) solution of the product of Step C1 (6.90 g 0.0377 mol) in dry dichloromethane (125 ml) under dry nitrogen. The stirred mixture was allowed to warm to room temperature overnight. Water was carefully added and a yellow precipitate was produced. The product was extracted twice into ether and the combined organic extracts were washed with water and dried. The solvent was removed in vacuo. Yield 6.40 g (100%) mp 156°–157° C.

Step C3

The procedure was as described for Step A2 above. Quantities: N-phenyltriflamide (9 g 0.024 mol), product of Step C2 (4 g 0.024 mol), triethylamine (4.9 g 0.049 mol). Yield 7.20 g (99%) mp 93°–94° C.

Step C4

The procedure for the boronic acid coupling step was as for Step B1 using the product of Step C3 instead of the bromonaphthalene and lithium chloride was added with the TTPP. Quantities: product of Step C3 (0.53 g 1.76 mmol), 4-n-butyloxphenylboronic acid (0.45 g 2.32 mmol) prepared as on Page 30–31 of WO 89/02425, TTPP (0.13 g 0.11 mmol), lithium chloride (0.22 g 5.22 mmol). The crude product was purified by column chromatography (silica gel/petroleum fraction (bp 40°–60° C.) -dichloromethane 1:1) to give a colourless solid which was recrystallised from hexane-dimethoxyethane ((1:1) to yield colourless crystals. Yield 0.30 9 (58%).

By analogous methods the compounds:

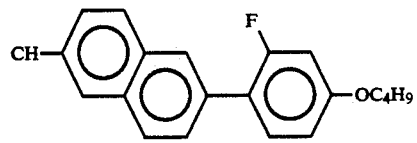

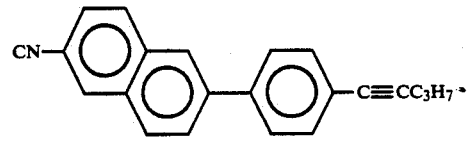

were prepared. The 4-butyloxy-2-fluorophenylboronic acid was prepared as described on Page 34–35 of WO 89/02425. The 4-pent-1-ynylphenylboronic acid was prepared as below.

A solution of n-butyllithium (7.8 ml 10M in hexane 0.078 mol) was added dropwise to a stirred, cooled (−5° to 0° C.) solution of pent-1-yne (5.28 g 0.078 mol) in dry THF (50 ml) under dry nitrogen. This mixture was stirred for 10 minutes and then a solution of dry zinc chloride (10.80 g 0.079 mol) in dry THF (100 ml) was added dropwise at −5° to 0° C. The mixture was stirred at room temperature for 15 minutes and a solution of para-iodobromobenzene (5.28 g 0.078 mol) in dry THF (100 ml) was added dropwise at −5° to 0° C. followed by the addition of TTPP (2.31 g 2.0 mmol). The mixture was stirred overnight and then poured into 10% hydrochloric acid.

The product was extracted twice into ether and the combined ethereal extracts were washed with aqueous sodium hydrogen carbonate and dried. The solvent was removed in vacuo. Yield 14.20 g (82%).

This 1-bromo-4-pent-1-ynylbenzene (13.45 g 0.06 mol) into the boronic acid in 91% yield using the same method as used in Step 1B on Page 31 of WO 89/02425. Quantities: magnesium (1.7 g 0.07 mol), tri-isopropyl borate (23 g 0.12 mol).

EXAMPLE 4—ROUTE D USED TO PREPARE

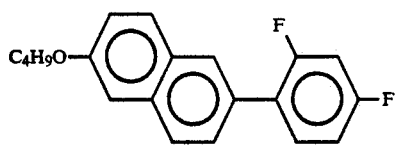

Step D1

N-butyllithium (12.40 ml 2.5M in hexane 0.031 mol) was added dropwise to a stirred, cooled (−78° C.) solution of 2-bromo-6-butoxynaphthalene (from Step A1) (8.60 g 0.031 mol) in dry THF (60 ml) under dry nitrogen. The reaction mixture was maintained under these conditions for 2.5 hours and then a previously cooled solution of tri-isopropyl borate (12 g 0.064 mol) in dry THF (50 ml) was added dropwise at −78° C. The mixture was allowed to warm to room temperature overnight and then stirred for one hour with 10% hydrochloric acid (80 ml). The product was extracted twice into ether and the combined ethereal extracts were washed with water and dried. The solvent was removed in vacuo to yield a colourless solid. Yield 8.5 g (100%).

Step D2

The coupling of the boronic acid (2.27 g 9.30 mmol) from Step D1 with 1-bromo-2,4-difluorobenzene (known) (1.37 g 7.10 mmol) was carried out as for Step B1 above using TTPP (0.26 g 0.23 mmol). The product was recrystallised from ethanol to yield colourless crystals. Yield 1.40 g (63%).

Using analogous procedures and known 4-bromo-3-fluoro-trifluoromethyl benzene, 1-bromo-3,4-difluorobenzene and para-bromofluorobenzene the compounds:

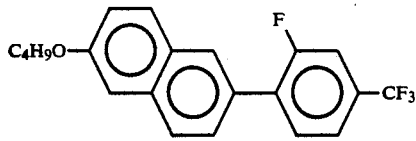

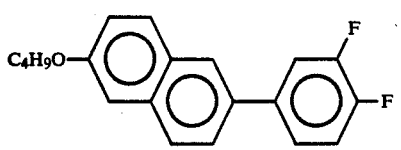

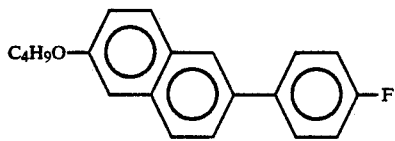

were prepared.

EXAMPLE 5—PROPERTIES OF COMPOUNDS PREPARED

TABLE 1

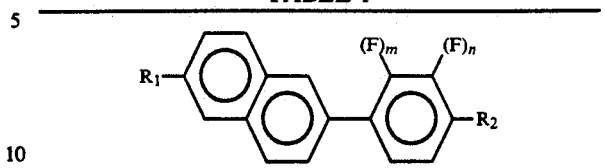

| | $R_1$ | $R_2$ | m | n | Liquid Crystal Transitions (°C.) |
|---|---|---|---|---|---|
| 1.1* | n-C8H17O | n-C5H11 | 1 | 1 | K 36 Sc 44.5 $S_A$ 75 N 83.5 I |
| 1.4 | n-C4H9O | F | 0 | 0 | K 128.5 (N 112.9) I |
| 1.5 | n-C4H9O | F | 1 | 0 | K 72 (N 63.0) I |
| 1.6 | n-C4H9O | F | 0 | 1 | K 81.5 N(42.0) I |
| 1.7 | n-C4H9O | CF3 | 1 | 0 | K 73.5 $S_A$ 105.5 I |
| 1.12 | n-C3H7C≡C | n-C4H9O | 1 | 0 | K 68.5 N 106.5 I |

*This compound showed a birefringence Δn = 0.19 at 20° C.

TABLE 2

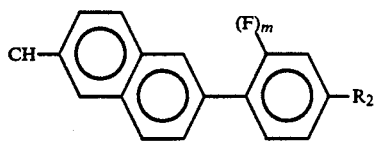

| | $R_2$ | m | Liquid Crystal Transitions (°C.) |
|---|---|---|---|
| 1.9 | OC4H9 | 0 | K 98.5 N 167.5 I |
| 1.10 | OC4H9 | 1 | K 64.5 N 129.5 I |
| 1.11 | C≡CC3H7 | 0 | K 113 N 193 I |

These properties indicate that phenylnaphthalenes of formula I have useful nematic and/or smectic C liquid crystalline properties, showing these useful phases over a broad temperature range.

EXAMPLE 6—FERROELECTRIC Sc* LIQUID CRYSTAL MIXTURE

A mixture was prepared having the composition:

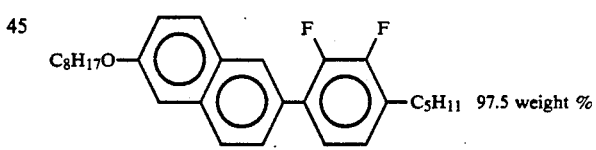 97.5 weight %

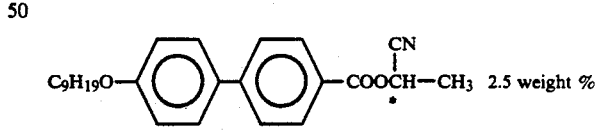 2.5 weight %

This mixture showed the liquid crystal transitions:

K 5 Sc* 33 $S_A$ 75 N 80.5 I

The mixture showed spontaneous polarisation Ps (nC cm$^{-2}$) and Sc* cone angles as listed below:

TABLE 3

| Temp (°C.) | Ps (nC cm$^{-2}$) | Cone Angle (°) |
|---|---|---|
| 32 | 0.1 | 3.5 |
| 30 | 1.3 | 6.5 |
| 28 | 1.8 | 8.5 |
| 25 | 2.2 | 10.5 |
| 20 | 2.8 | 11 |

TABLE 3-continued

| Temp (°C.) | Ps (nC cm$^{-2}$) | Cone Angle (°) |
|---|---|---|
| 18 | 2.9 | |
| 15 | 3.1 | |
| 10 | 3.3 | |
| 5 | 3.5 | |

Using a 2.0 μm cell at 25° C. the switching speed of this mixture was measured as below:

TABLE 4

| Voltage (V peak) | Response Time (μ sec) |
|---|---|
| 20 | 120 |
| 30 | 76 |
| 40 | 54 |
| 50 | 45 |
| 60 | 37 |
| 70 | 32 |

The mixture is therefore a fast switching ferro-electric Sc* material showing a room temperature Sc* phase.

We claim:

1. An optically inactive phenylnaphthalene of the formula I:

$R_1$—[naphthalene]—[phenyl-(F)$_m$]—$R_2$     formula I wherein $R_1$ and $R_2$ are selected from $C_{1-15}$ alkyl, alkoxyl, perfluoroalkyl, perfluoroalkoxyl and alkynyl, $R_1$ may also be CN and $R_2$ may also be fluorine, CN or NCS; m is 0, 1 or 2 provided that if $R_1$ is alkyl or alkoxyl and $R_2$ is alkyl, alkoxyl, perfluoroalkyl or CN than m is 1 or 2.

2. Phenylnaphthalenes according to claim 1 wherein $R_1$ and $R_2$ are independently selected from alkyl and alkoxyl and m is 1 or 2.

3. Phenylnaphthalenes according to claim 2 having a formula:

$R_1$—[naphthalene]—[phenyl with F,F]—$R_2$

4. An optically inactive phenylnaphthalene of the formula:

$R_1$—[naphthalene]—[phenyl-(F)$_m$]—$R_2$     formula I wherein $R_1$ is $C_{1-15}$ alkyl or alkoxyl, $R_2$ is fluorine and m is 0, 1 or 2.

5. Phenylnaphthalenes according to claim 4 characterised by a formula:

$R_1$—[naphthalene]—[phenyl]—F

6. Phenylnaphthalenes according to claim 4 characterised by a formula:

$R_1$—[naphthalene]—[phenyl-F]—F $R_1$—[naphthalene]—[phenyl-F]—F

7. An optically inactive phenylnaphthalene of the formula:

$R_1$—[naphthalene]—[phenyl-(F)$_m$]—$R_2$     formula I wherein $R_1$ is CN, $R_2$ is $C_{1-15}$ alkyl, alkoxy or alkynyl and m is 0, 1 or 2.

8. Phenylnaphthalenes according to claim 7 having a formula:

CH—[naphthalene]—[phenyl]—$R_2$ where $R_2$ is alkyl or alkoxyl.

9. Phenylnaphthalenes according to claim 7 having a formula:

CN—[naphthalene]—[phenyl-F]—$R_2$ where $R_2$ is alkyl or alkoxyl.

10. Phenylnaphthalenes according to claim 7 having a formula:

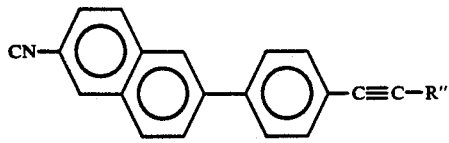

wherein R'' is alkyl.

11. An optically inactive phenylnaphthalene of the formula:

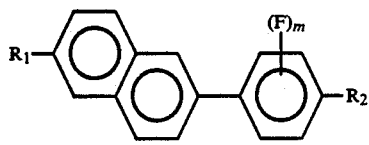

formula I wherein $R_1$ is alkynyl and $R_2$ is alkyl or alkoxyl.

12. Phenylnaphthalenes according to claim 11 having a formula:

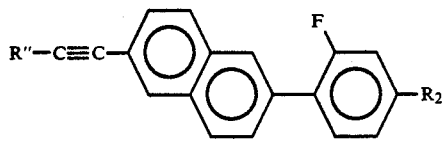

wherein $R_2$ is alkyl or alkoxy and R'' is alkyl.

13. Phenylnaphthalenes according to claim 1 having a formula selected from:

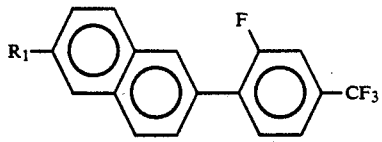

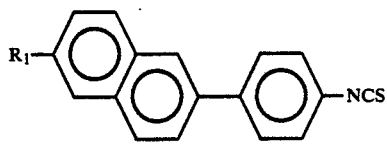

wherein $R_1$ is alkyl or alkoxyl.

14. Liquid crystal material being a mixture of at least 2 component compounds, at least one of which is phenylnaphthalene of formula I as claimed in claim 1.

15. Liquid crystal material according to claim 14 wherein it is a nematic material that contains 5–50 weight % of phenyl naphthalene(s) of formula I in which $R_1$ is alkyl or alkoxyl and $R_2$ is fluorine, or $R_1$ is alkynyl and $R_2$ is alkyl or alkoxyl, or $R_1$ is CN and $R_2$ is alkyl, alkoxyl or alkynyl, and in that the material contains 50–95 weight % of compound(s) of formula IIA, IIB or IIC:

IIA

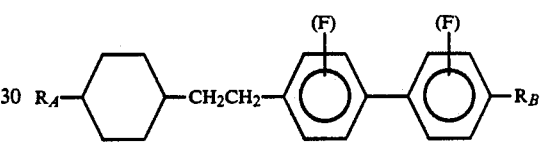
IIB

IIC wherein $R_A$ and $R_B$ are independently $C_{1-10}$ alkyl or n-alkoxy and (F) indicates that the compounds of IIB have a single lateral fluorine phenyl substituent.

16. Liquid crystal material according to claim 14 wherein it is a ferro-electric chiral smectic C liquid crystal material that contains 1–99 weight % of phenylnaphthalene(s) of formula I in which $R_1$ and $R_2$ are selected from n-alkyl or n-alkoxyl and m is 1 or 2 and in that the material contains 1–20 weight % of optically active compound(s), the total being 100 weight %.

17. Material according to claim 16 wherein m is 2, the fluorines being in the 2, 3 positions.

* * * * *